(12) United States Patent
Faul et al.

(10) Patent No.: US 6,497,134 B1
(45) Date of Patent: Dec. 24, 2002

(54) CALIBRATION OF AN INSTRUMENT

(75) Inventors: Ivan Faul, Boulder, CO (US); Jesse Dean Paylor, Frederick, CO (US)

(73) Assignee: Image Guided Technologies, Inc., Boulder, CO (US)

( * ) Notice: Subject to any disclaimer, the term of this patent is extended or adjusted under 35 U.S.C. 154(b) by 0 days.

(21) Appl. No.: 09/525,895

(22) Filed: Mar. 15, 2000

(51) Int. Cl.$^7$ ............................................... G01D 18/00
(52) U.S. Cl. ..................... 73/1.81; 73/1.75; 73/1.79; 606/130; 600/427; 600/429
(58) Field of Search ................. 606/130, 1; 600/417, 600/426, 424, 427, 429; 73/1.79, 1.81, 1.75

(56) References Cited

U.S. PATENT DOCUMENTS

| | | | |
|---|---|---|---|
| 4,323,459 A | 4/1982 | Quinlan | 210/700 |
| 4,396,945 A | 8/1983 | DiMatteo et al. | 358/107 |
| 4,722,056 A | 1/1988 | Roberts et al. | 364/413 |
| 4,869,247 A | 9/1989 | Howard, III et al. | 128/303.1 |
| 4,923,459 A | 5/1990 | Nambu | 606/130 |

(List continued on next page.)

FOREIGN PATENT DOCUMENTS

| | | | | |
|---|---|---|---|---|
| DE | 3904595 | 4/1990 | | A61B/19/00 |
| EP | 326768 | 8/1989 | | A61B/19/00 |
| JP | 3267054 | 11/1991 | | A61B/19/00 |
| JP | 6282889 | 10/1994 | | G11B/11/10 |
| JP | 6282890 | 10/1994 | | G11B/11/10 |
| WO | WO 90/05494 | 5/1990 | | A61B/17/22 |
| WO | WO 94/23647 | * 10/1994 | | A61B/5/05 |
| WO | WO 00/39576 | 7/2000 | | |

OTHER PUBLICATIONS

Applied Neurophysiology, Journal of Stereotactic and Functional Neurosurgery, Proceedings of the Meeting of the American Society for Stereotactic and Functional Neurosurgery, Montreal, Quebec, (Jun. 3–6, 1987) Jan. 1998.

Stereotactic & Functional Neurosurgery vol. 53, No. 3, (1989) pp. 197–201.

Journal of Ultrasound in Medicine vol. 9, No. 9, (Sep. 90), pp. 525–532.

Ultrasound in Neurosurgery J.M. Rubin et al. ISBN: 0881675490, pp. 47–58.

Stereotactic & Functional Neurosurgery vol. 54–55, (1990), pp. 419, 422, 423, 471–476, 488–492, 493–496, 497, 498, 500.

(List continued on next page.)

*Primary Examiner*—Michael J. Milano
*Assistant Examiner*—Daniel Jacob Davis
(74) *Attorney, Agent, or Firm*—McCracken and Frank

(57) ABSTRACT

A system for calibrating an error between the location of a feature of an object as determined by indirect calculation compared to as determined by physical measurement in order to be able to use this determined error to correct the location of the feature as determined by calculation in actual use in the field. This error is found by calculating the position and orientation of the object, having energy emitters disposed thereon, in a plurality of orientations and positions relative to a reference frame, but with the feature in a substantially constant position relative to the reference frame; calculating the locations of the feature of the object from these calculated positions and orientations; averaging these calculated locations; determining the location of the feature by physical measurement thereof in relation to the physical locations of the emitters; and comparing the calculated average location with the physically measured loacation to arrive at the error.

2 Claims, 2 Drawing Sheets

U.S. PATENT DOCUMENTS

| | | | |
|---|---|---|---|
| 4,945,914 A | 8/1990 | Allen | 128/653 R |
| 4,951,653 A | 8/1990 | Fry et al. | 128/24 A |
| 4,991,579 A | 2/1991 | Allen | 128/653 R |
| 5,016,639 A | 5/1991 | Allen | 128/653 R |
| 5,094,241 A | 3/1992 | Allen | 128/653.1 |
| 5,097,839 A | 3/1992 | Allen | 128/653.1 |
| 5,119,817 A | 6/1992 | Allen | 128/653.1 |
| 5,138,563 A * | 8/1992 | Debitsch et al. | 702/95 |
| 5,142,930 A | 9/1992 | Allen et al. | 74/469 |
| 5,178,164 A | 1/1993 | Allen | 128/898 |
| 5,186,174 A | 2/1993 | Schlondorff et al. | 128/653.1 |
| 5,198,877 A | 3/1993 | Schulz | 356/375 |
| 5,211,164 A | 5/1993 | Allen | 128/653.1 |
| 5,222,499 A | 6/1993 | Allen et al. | 128/653.1 |
| 5,230,338 A | 7/1993 | Allen et al. | 128/653 |
| 5,309,101 A | 5/1994 | Kim et al. | 324/309 |
| 5,394,875 A | 3/1995 | Lewis et al. | 128/660.09 |
| 5,397,329 A | 3/1995 | Allen et al. | 606/73 |
| 5,467,634 A * | 11/1995 | Brady et al. | 340/937 |
| 5,494,034 A | 2/1996 | Schlondorff et al. | 128/653.1 |
| 5,515,160 A | 5/1996 | Schulz et al. | 356/241 |
| 5,551,429 A | 9/1996 | Fitzpatrick et al. | 128/653.1 |
| 5,575,794 A | 11/1996 | Walus et al. | 606/116 |
| 5,383,454 A | 12/1996 | Bucholz | 128/653.1 |
| 5,588,430 A * | 12/1996 | Bova et al. | 378/204 |
| 5,590,215 A | 12/1996 | Allen | 382/128 |
| 5,595,193 A | 1/1997 | Walus et al. | 128/898 |
| 5,617,857 A | 4/1997 | Chader et al. | 128/653.1 |
| 5,622,170 A | 4/1997 | Schulz | 128/653.1 |
| 5,638,819 A | 6/1997 | Manwaring et al. | 128/653.1 |
| 5,665,896 A * | 9/1997 | McMurtry | 73/1.75 |
| 5,695,501 A | 12/1997 | Carol et al. | 606/130 |
| 5,704,897 A | 1/1998 | Truppe | 600/117 |
| 5,711,299 A | 1/1998 | Manwaring et al. | 128/653.1 |
| 5,730,130 A | 3/1998 | Fitzpatrick et al. | 128/653.1 |
| 5,752,513 A | 5/1998 | Acker et al. | 128/653.1 |
| RE35,816 E | 6/1998 | Schulz | 356/376 |
| 5,769,789 A | 6/1998 | Wang et al. | 600/414 |
| 5,797,924 A | 8/1998 | Schulte et al. | 606/130 |
| 5,799,099 A | 8/1998 | Wang et al. | 382/131 |
| 5,816,096 A * | 10/1998 | Ng et al. | 73/1.79 |
| 5,851,183 A | 12/1998 | Bucholz | 600/425 |
| 5,871,445 A | 2/1999 | Bucholz | 600/407 |
| 5,891,034 A | 4/1999 | Bucholz | 600/426 |
| 5,891,157 A | 4/1999 | Day et al. | 606/130 |
| 5,907,395 A | 5/1999 | Schulz et al. | 356/139.03 |
| 5,916,164 A | 6/1999 | Fitzpatrick et al. | 600/426 |
| 5,921,992 A | 6/1999 | Costales et al. | 606/130 |
| 5,954,648 A | 9/1999 | Van Der Brug | 600/411 |
| 5,970,499 A | 10/1999 | Smith et al. | 707/104 |
| 5,987,349 A | 11/1999 | Schulz | 600/427 |
| 6,073,044 A | 6/2000 | Fitzpatrick et al. | 600/426 |
| 6,081,336 A | 6/2000 | Messner et al. | 356/375 |
| 6,112,113 A | 8/2000 | Van Der Brug et al. | 600/427 |
| 6,112,423 A * | 9/2000 | Sheehan | 33/502 |
| 6,161,033 A * | 12/2000 | Kuhn | 600/407 |
| 6,235,038 B1 * | 5/2001 | Hunter et al. | 600/417 |
| 6,261,300 B1 * | 7/2001 | Carol et al. | 600/417 |
| 6,267,769 B1 * | 7/2001 | Truwit | 606/1 |
| 6,267,770 B1 * | 7/2001 | Truwit | 600/417 |
| 6,298,262 B1 * | 10/2001 | Franck et al. | 600/426 |
| 6,332,891 B1 * | 12/2001 | Himes | 606/130 |
| 6,377,839 B1 * | 4/2002 | Kalfas et al. | 128/897 |
| 2001/0045021 A1 * | 11/2001 | Matsuda et al. | 33/502 |

OTHER PUBLICATIONS

British Journal of Neurosugery vol. 4, No. 3, (1990), pp. 193–197.

IEEE Computer Graphics & Applications vol. 10, No. 3, (May 90), pp. 43–51.

Journal of Neurosurgery vol. 72, No. 2, (Feb. 90), pp. 355a.

IEEE Engineering in Medicine & Biology Society—Proceedings of 11$^{th}$ Annual International Conference, (1989), pp. 925, 926–929.

British Journal of Neurosurgery vol. 3, No. 5, (1989), pp. 561–568, 569–574.

British Journal of Neurosurgery vol. 3, No. 3, (1989), pp. 327–331.

Acta Neurochirurgica Supplementum 46, (1989), pp. 112–114.

Journal of Neurosurgery vol. 65, No. 4, (Oct. 86), pp. 550–554, 557–559.

Journal of Neurosurgery vol. 57, No. 2, (Aug. 82), pp. 157–163.

Neurosurgery vol. 10, No. 5, (May 82), pp. 580–586.

Neurosurgery vol. 10, No. 3, (Mar. 82), pp. 375–379.

Guilded Brain Operations E.A. Spiegel ISBN: 3805534515, (1982), pp. 23, 25, 28.

American Journal of Neuroradiology vol. 2, No. 2, (Mar./Apr. 81), pp. 181–184.

Neurosurgery vol. 8, No. 1, (Jan. 81), pp. 72–82.

Surgical Neurology vol. 14, No. 6, (Dec. 80), pp. 451–464.

Investigative Radiology vol. 15, No. 4, (Jul./Aug. 80), pp. 308–312.

Applied Neurophysiology vol. 43, No. 3–5, (1980), pp. 170–171, 172–173, 174–175.

Neurosurgery vol. 3, No. 2, (Sep./Oct. 78), pp. 157–161.

Birkfellner et al., "Evaluation and Detection of Systematic Distortions in DC–pulsed Electromagnetic Position Sensing Devices," *Elsevier Science B.V.*, 1998, pp. 927–928.

Birkfellner et al., "Systematic Distortions in Magnetic Position Digitizers," *Med. Phys.* 25(11), pp. 2242–2248 (Nov. 1998).

Livingston et al., "Magnetic Tracker Calibration for Improved Augmented Reality Registration," *Presence*, vol. 6, No. 5, pp. 532–546 (Oct. 1997).

State et al., "Superior Augmented Reality Registration by Integrating Landmark Tracking and Magnetic Tracking," Proceedings of SIGGRAPH 96 (New Orleans, LA, Aug. 4–9, 1996). In *Computer Graphics* Proceedings, Annual Conference Series, pp. 429–438.

Birkfellner et al., "Calibration of Tracking Systems in a Surgical Environment," *IEEE Tansactions on Medical Imaging*, Nov. 17, 1998, pp. 1–6.

Birkfellner et al., "Evaluation of Magnetic Position Digitizers for Computer Assisted Surgery," *Comput. Aided Surg.* 2(3/4), 225 (1997).

International Search Report dated Aug. 15, 2001, Int'l. Appl. No. PCT/US01/02166.

* cited by examiner

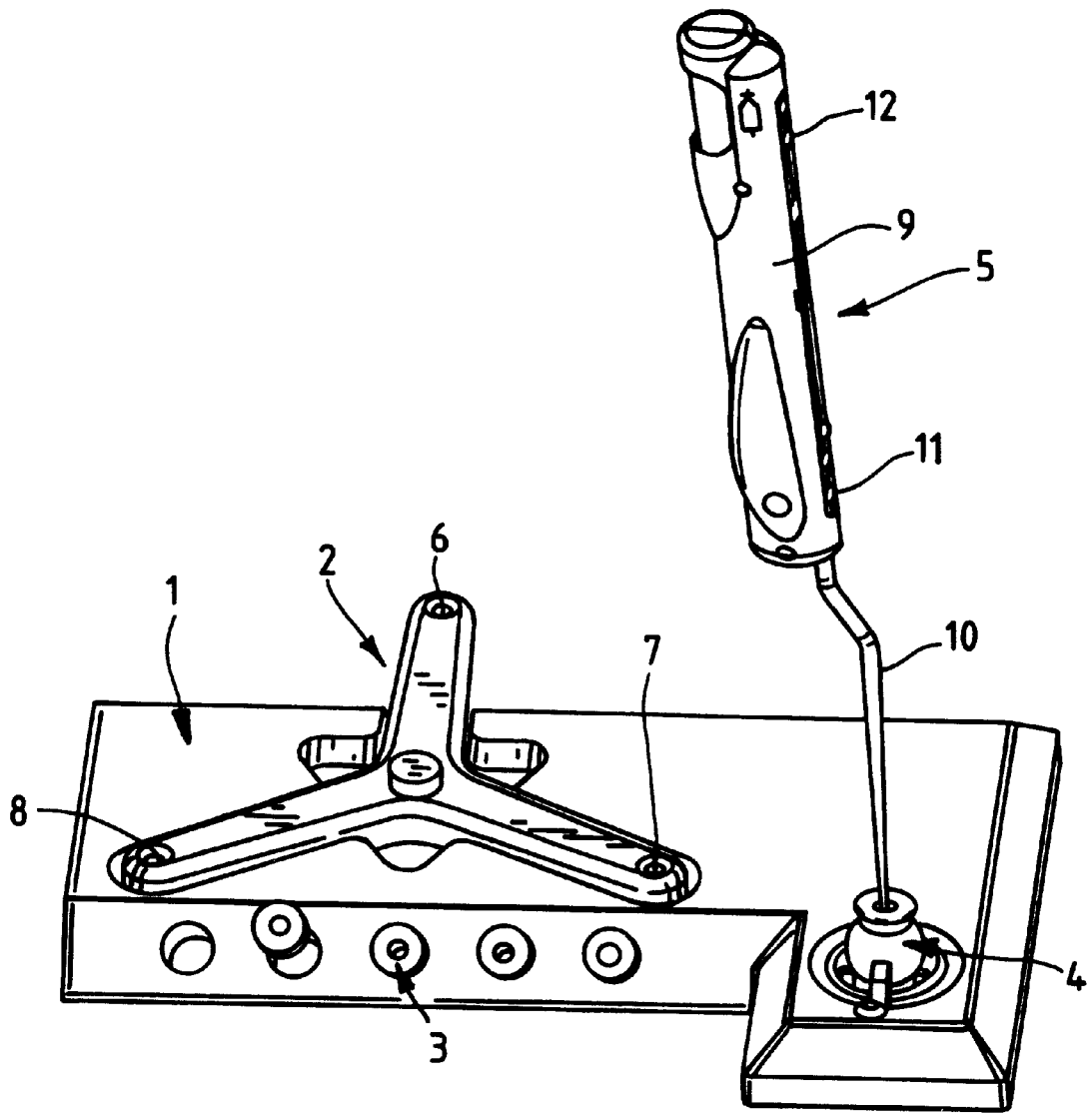

CALIBRATION OF AN INSTRUMENT

FIELD OF THE INVENTION

This invention relates to an improvement in systems for tracking the position and orientation of substantially rigid bodies in (3-D) space, such as medical probes. It more particularly relates to a method of calibrating the geometry of the body in anticipation of determining its position and orientation is space.

DESCRIPTION OF THE BACKGROUND ART

Various methods and systems are known that have the ability to track the position and orientation of bodies in a spatial volume relative to an arbitrary global 3-D coordinate system. Multiple emitters, such as for example emitters or reflectors of electromagnetic radiation, disposed in geometrically known locations relative to the body being tracked, can themselves be tracked, by suitable electromagnetic radiation sensors for example. Various combinations of multiple emitters and/or receivers can triangulate the location of the emitters/reflectors relative to the receivers through the use of appropriate algorithms. These determined emitter locations relative to the sensor(s) can be converted, by appropriate algorithms, to determined locations of the emitters on the object, and these locations can in turn be converted, by appropriate algorithms, to reveal the position and orientation of the object in the defined three dimensional (3-D) space. For example, the bodies being tracked can be hand-held probes, moveable inanimate objects, or semi-rigid portions of human or other animal anatomy.

OBJECTS AND SUMMARY OF THE INVENTION

An objective of this invention is to provide a method of calibrating an object, such as a surgical instrument, despite having limited knowledge of the geometry of the object/instrument.

Another object of this invention is to provide a method and apparatus for calibrating one or more specific features of an object/instrument.

A further objective of the invention is to provide a method of verifying the geometry of an instrument, especially a surgical instrument, to determine the location of a particular feature of an instrument relative to other features of the instrument, with knowledge of the geometry of the instrument.

It is a more specific object of this invention to calibrate the location of the tip of a surgical probe relative to the locations of plural emitters/reflectors disposed on said probe remote from the tip thereof.

Other and additional objects will become apparent from a consideration of this entire specification, the drawing and the appended claims.

In accord with and fulfilling these objects, one aspect of the instant invention is an apparatus that is suited to calibrating the location of a particular geometric feature of an object relative to the locations of plural energy emitters disposed on that object and spaced from the feature. The apparatus of this invention comprises an assembly of:

A. a reference frame, comprising plural emitters;

B. a pivotable gimbal, adapted to receive the object being calibrated;

C. a mounting block to which the reference frame and the gimbal are attached in a manner such that the spatial relationship between the gimbal and the reference frame is substantially constant regardless of the pivoting of the gimbal and such that the geometric feature of the object, whose position is being determined, resides in a substantially fixed location in said gimbal relative to the reference frame;

D. plural energy emitters and/or reflectors disposed in non-colinear, known locations on the reference frame;

E. an object

F. plural energy emitters and/or reflectors disposed in known locations on the object remote from said feature;

G. at least one energy sensor spaced from said mounting block;

H. means, such as a computer, adapted to determine the locations of said energy emitters/reflectors on said object relative to the reference frame;

I. means, such as a computer, adapted to determine the locations of said feature relative to said reference frame and means, such as the same or a different computer, adapted to compare the location of said feature as determined in I with the location of said feature as determined from the geometry of said object and to thereby determine an error between the two determined locations of the feature; and J. collets for adapting the gimbal to different size probes.

The calibration method comprises:

A. disposing a reference frame, having plural, non-colinear energy emitters/reflectors disposed thereon, in a known spatial relationship to a pivotable gimbal such that an accessible location on said gimbal is substantially always in a fixed spatial relationship to said reference frame regardless of the pivoting of the gimbal;

B. disposing an object, comprising a geometric feature and plural energy emitters/reflectors, in operative relationship to said gimbal such that said feature is disposed in known spatial relationship to said accessible location;

C. radiating energy from said emitters/reflectors to at least one energy sensor;

D. determining an angle subtended between energy radiated from at least some of the emitters/reflectors and at least one reference line;

E. calculating the locations of the emitters/reflectors on said object relative to said reference frame;

F. calculating the location of the feature as a function of the locations of emitters determined in step E;

G. measuring the location of the feature as a geometric function of the physical locations of the emitters on the object; and H. comparing the locations of the feature as determined in steps F and G to generate an error value.

The calibration of the feature of the object is accomplished by placing the object E in operative relation to the gimbal B with the feature (not shown) at a point that does not change its location relative to the position and orientation of the reference frame A as the gimbal is pivoted. The gimbal B is successively pivoted to a plurality of positions/orientations while maintaining the feature in the same relative location. The location of the feature is repeatedly calculated, from the spatial relationships between the object emitters F and the reference frame emitters D, with the object in a sufficient number of different positions/orientations to provide a statistically significant amount of data. These plural determined locations are then averaged to provide a calculated location of the feature. This calculated location is then compared with the location of the feature as physically measured relative to the locations of object emitters. The difference between these calculated and measured values is an error value. This error value is then applied to the location of the feature as it is later determined from calculations made in the field of use.

According to this invention, the energy emitters or reflectors F can be disposed on the object E and the reference frame A and energy transmitted from the frame and the object, respectively to the sensor(s) G. In the alternative the sensors may be located on the reference frame and/or the object, and the emitters/reflectors disposed a distance from the object/reference frame assembly.

The sensor(s) must have a means for differentiating between transmitted energy related to the reference frame and the transmitted energy related to the object. This transmission may be simultaneous, in which case the energy associated with the frame must be of a different wave length or character, or have some identifying signal imposed (modulated) thereon, that is distinguishable from the energy being transmitted that is associated with the object. Further, the specific emitters/reflectors/sensors must be differentiatable one from the other so that the system known which point it is calculating. Another means of differentiating is to use transmission of energy that is sequential, with the several emitters associated with the frame transmitting in a sequence and the several emitters associated with the object transmitting in sequence. A combination of sequencing and energy wave length can be used. Other differentiating means may be used as desired. Where the transmissions are sequential in any pattern, it is important that the position and orientation of the object, the reference frame and the sensor(s) be maintained substantially constant between each pair of these elements so that the calculated locations of the several emitters can be compared in a meaningful manner.

The error values determined according to this invention are used to correct the location of the feature when that location is calculated in the field during actual use of the object after calibration. In this way, the calculated location of the feature, determined as a function of the calculated locations of the several energy emitters or reflectors, and transmitted to the energy sensor(s), during actual use can be adjusted so as to make the determined location of the feature more accurate.

In a preferred embodiment of this invention, a surgical probe having a handle, a tip and plural energy emitters/reflectors disposed thereon is calibrated using this apparatus. This preferred method comprises inserting the tip of the probe into the gimbal so that it rests at the rotational axis of the gimbal. The gimbal is then rotated such that the handle of the probe, with the emitters/reflectors thereon, pivots around the rotational axis of the gimbal and therefore around the location of the feature being determined. A measuring system calculates the positions of the probe relative to the reference frame by taking plural readings of the locations of the several emitters/reflectors as the probe/gimbal is rotated and calculating the position and orientation of the probe. From the data showing the locations of the several emitters relative to each other, a mathematical software routine (an algorithm) calculates the tip location relative to the rest of the probe. The error between the directly physically measured and indirectly calculated tip locations is then used to correct the calculated locations of the probe tip as determined in the field.

According to one aspect of this invention, a physically measured location of the feature of the object is stored, suitably in a computer. The feature of the object/instrument, whose location is to be determined, is inserted into the fixed relationship to the rotational origin (the point in or on the gimbal that does not move relative to the reference frame and mounting block) and the instrument rotated such that it pivots around the rotational origin of the gimbal. The indirect measuring system (calculation) described herein calculates and records the several positions and orientations of the object by taking readings of the locations of the plural energy emitters as the gimbal is pivoted. A mathematical software routine (an algorithm) calculates the tip location relative to the rest of the instrument, and then the calculated tip location is compared with the stored physically measured tip location. A difference between these values is determined/computed and this is referred to as the error. The magnitude of the error is a factor that is used to evaluate how the calibrated instrument will be utilized. However, the usual use of this error factor is to correct the locations of the tip as calculated from field data.

BRIEF DESCRIPTION OF THE DRAWINGS

The accompanying drawing the figures illustrate a preferred embodiment of the present invention.

FIG. 2 id similar to FIG. 1 with an object being clibrated shown in operative position.

The components apparatus shown in the figure are:

Figure 1:
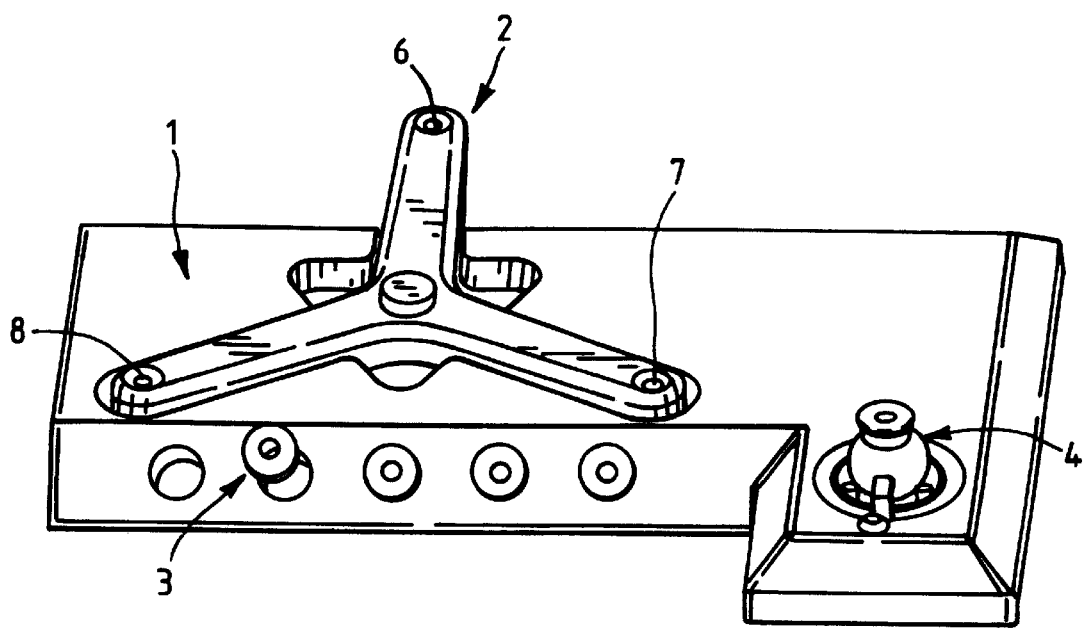
FIG. 1 is a perspective view of one embodiment of the apparatus of this invention.

1. A mounting block;
2. An image guided reference frame;
3. Size adapting collets;
4. A pivoting gimbal;
5 An object being investigated
6, 7 and 8 Reference frame emitters; and
9 Object handle;
10 Object shaft; and
11 and 12 Object handle emitters Referring now to the drawing, a mounting block 1 has means for accepting and maintaining a reference frame 2 and a rotatable gimbal 4 in fixed spatial relationship to each other. The reference frame has three non-colinear energy emitters/reflectors 6, 7 and 8. The object 5 under investigation is illustrated in the drawing by a surgical probe. The probe is made up of a handle 9 and a shaft 10. The shaft terminates at its distal end in a tip (not shown). This tip is the feature of the object/probe whose location is to be determined. In the drawing, the specific location of this tip feature is not shown because it is located within the gimbal. Suffice it to say that it is at the end of the shaft and is in fixed spatial relationship with the origin of the gimbal.

In practice, the instant assembly is disposed in a three dimensional volume that is defined by a three dimensional coordinate system. A plurality of sensors, adapted to receive energy radiated from the emitters elements (not shown) are provided in known spatial relationship to that three dimensional coordinate system. At least some of the sensors are always in line of sight in relation to the emitters. As the object is moved along with the gimbal, according to this invention, the specific sensor(s) that are operative may change.

This invention has been described in relation to energy emitters disposed on the reference frame and the object and energy sensors disposed within the three dimensional volume a distance from the frame and the object. It is considered to be within the scope of this invention to reverse this.

The sensors may be disposed on the reference frame and the object and the emitters/reflectors disposed elsewhere in the three dimensional volume. The operation of the system will not be significantly different. Reference has been made to energy emitters/reflectors. It is contemplated that either true emitters of energy, or reflectors of energy, or a combination of both can be used in this invention. If reflectors are used, it will be apparent that some source of radiating energy will then have to be impinged upon the reflectors. There may be one or a plurality of such sources.

The preferred radiating energy used in this invention is electromagnetic radiation, such as visible or infra red light. However, the operation of the instant calibration system will be substantially the same even if other form of energy, such as for example ultra sound, is employed. Of course, a combination of several species of energy is contemplated.

The preferred form of this invention uses infra red electromagnetic radiation. The emitters may be infra red light emitting diodes (LEDs) or they may be the ends of light guides (optical fibers) having a light source that is remote from the emitters themselves. Each emitter may have a separate light source or plural emitters my be manifolded off a single light source. Multiple light sources may power a single emitter/reflector.

It is contemplated that a plurality of sensors will be employed in the practice of this invention. The minimum number of sensors will be a function of the character of the sensor(s). For example, if a 1-D sensor is being used, such as a single row of pixels, it will be preferred to employ at least three such sensors in order to accurately determine the position and orientation of the reference frame and the object. However, if a 2-D sensor is being used, a minimum of two sensors are adequate. Obviously, if a 3-D sensor is being used, only a single sensor is absolutely required, subject always to the line of sight requirements for electromagnetic energy use as set forth above.

What is claimed is:

1. An apparatus adapted to calibrate the location of a feature of an object relative to the locations of plural energy emitters disposed on that object and spaced from the feature, where the apparatus comprises an assembly of:

A. a reference frame, comprising plural energy emitters;
   B. a pivotable gimbal having an origin that is adapted to be in substantially fixed spatial relationship to said reference frame regardless of pivoting of said gimbal, wherein said gimbal is adapted to receive said object being calibrated such that the feature, whose location is being determined, resides at said origin;
   C. means to maintain the reference frame and the origin of the gimbal in substantially constant spatial relationship regardless of the pivoting of the gimbal;
   D. said object being calibrated comprising plural energy emitters and at least one feature in fixed structural relationship to and remote from said emitters;
   F. at least one energy sensor spaced from said emitters;
   G. means to radiate energy from said emitters to said sensor(s);
   H. computing means adapted to calculate the locations of said object energy emitters relative to the reference frame;
   I. computing means adapted to calculate the locations of said feature relative to said reference frame; and
   J. computing means adapted to compare the location of said feature as calculated in I with the location of said feature as physically measured on said object and to thereby determine an error between the calculated and measured location, respectively, of the feature.

2. A method of calibrating the location of a feature of an object comprising:

A. disposing a reference frame, having plural energy emitters disposed thereon, in spatial relationship to a pivotable gimbal having an accessible origin, wherein said origin is in known spatial relationship to said reference frame regardless of the pivoting of the gimbal;
   B. disposing an object, comprising a geometric feature and plural energy emitters, in operative relationship to said gimbal such that said feature is disposed at said origin;
   C. radiating energy from said emitters to at least one energy sensor;
   D. from said energy radiation, calculating the locations of at least some of the emitters on said object and on said reference frame, wherein the number of emitter locations determined is sufficient to calculate a spatial relationship between said object and said reference frame;
   E. from the locations of emitters determined in step D, calculating the location of the feature;
   F. physically measuring the location of the feature as a geometric function of the actual locations of the emitters on the object; and
   G. comparing the calculated and measured locations of the feature to generate an error value.

* * * * *